(12) United States Patent
Cui

(10) Patent No.: US 8,455,673 B2
(45) Date of Patent: Jun. 4, 2013

(54) WATER DISPERSIBLE SILANES

(75) Inventor: Ji Cui, Naperville, IL (US)

(73) Assignee: Nalco Company, Naperville, IL (US)

( * ) Notice: Subject to any disclaimer, the term of this patent is extended or adjusted under 35 U.S.C. 154(b) by 136 days.

(21) Appl. No.: 12/953,658

(22) Filed: Nov. 24, 2010

(65) Prior Publication Data

US 2011/0067599 A1 Mar. 24, 2011

Related U.S. Application Data

(62) Division of application No. 11/334,722, filed on Jan. 18, 2006, now Pat. No. 7,862,862.

(51) Int. Cl.
*C07F 7/10* (2006.01)
(52) U.S. Cl.
USPC ........................ 556/423; 106/287.11
(58) Field of Classification Search
None
See application file for complete search history.

(56) References Cited

U.S. PATENT DOCUMENTS

| 3,509,012 | A | * | 4/1970 | Marzocchi ..................... 523/213 |
| 4,140,830 | A | | 2/1979 | Williams et al. |
| 5,085,694 | A | * | 2/1992 | Cifuentes ......................... 106/3 |
| 5,209,871 | A | * | 5/1993 | Mason ........................... 252/500 |
| 5,270,428 | A | * | 12/1993 | Castellucci ..................... 528/38 |
| 5,750,197 | A | | 5/1998 | van Ooij et al. |
| 6,261,638 | B1 | | 7/2001 | van Ooij et al. |
| 6,416,869 | B1 | | 7/2002 | van Ooij et al. |
| 6,867,318 | B1 | | 3/2005 | Cui |
| 6,900,260 | B1 | | 5/2005 | Mangels et al. |
| 7,704,622 | B1 | * | 4/2010 | Meador et al. ................. 429/493 |
| 2003/0153777 | A1 | | 8/2003 | Wilkes et al. |

FOREIGN PATENT DOCUMENTS

| EP | 0570173 | 5/1993 |
| WO | 0112876 | 2/2001 |

* cited by examiner

*Primary Examiner* — Robert S Loewe
(74) *Attorney, Agent, or Firm* — Edward O. Yonter; Andrew D. Sorensen

(57) ABSTRACT

Disclosed and claimed is a composition that comprises a dispersion in a solvent of a compound comprising the reaction product of (1) a polyamine in which a plurality of amine groups are bonded to at least one radical comprising alkylene or arylene groups that separate the polyamine nitrogen atoms by at least four intermediate atoms in a chain, and (2) a silane which carries a plurality of silicon-bonded hydrolysable groups, and a silicon-bonded organic group that is covalently reactive with and which bonds with an amine group, to provide a reaction product molecule which comprises an average of at least about 2.5 of said silane groups per molecule. Some of these materials show superior advantage as a paint primer and some provide excellent corrosion resistance.

8 Claims, No Drawings

WATER DISPERSIBLE SILANES

CROSS REFERENCE TO RELATED APPLICATIONS

This application is a divisional application of U.S. application Ser. No. 11/334,722, "WATER DISPERSIBLE SILANES AS CORROSION-PROTECTION COATINGS AND PAINT PRIMERS FOR METAL PRETREATMENT," filed on Jan. 18, 2006, now U.S. Pat. No. 7,862,862, incorporated herein by reference in its entirety.

TECHNICAL FIELD OF THE INVENTION

This invention relates generally to compositions for improving paint adhesion. More specifically, the invention relates to a dispersion of a compound having a silicon-bonded hydrolyzable group or an alkyl group.

BACKGROUND OF THE INVENTION

Metals such as zinc, iron, chromium, zirconium, manganese, cobalt, nickel, titanium, and molybdenum in their oxide form, and phosphates thereof, have been used in metal pretreatment processes for almost a century, serving as an excellent base for applying a paint top coat, and also providing some protection against corrosion without paint. For aluminum pretreatment, hexavalent chromium is very popular, and its performance has been basically unparalleled by other known non-chrome alternatives. Unfortunately, because of the carcinogenic characteristic of hexavalent chromium, its uses are increasingly restricted in Europe and the United States. Besides health and environmental concerns, chromium adds financial burden to the aluminum pretreatment industry, for example the high expense in treating liquid waste discharge to remove it.

To address the above environmental and health-related issues related to hazardous metals, by this invention a typically metal-free, corrosion-resistant pretreatment coating is provided, being applicable to aluminum and its alloys, as well as zinc and its alloys, and magnesium and its alloys, as well as other metals. Thus, the coating may be applied to galvanized iron and steel components as well as to aluminum, magnesium and the like.

The coating of this invention is derived from a typically aqueous precursor solution, typically by dip-coating or spraying onto metal surfaces. The coating subsequently forms a cross-linked and typically hydrophobic film after a short duration of drying and crosslinking. The coating on metal exhibits excellent corrosion resistance, high thermal stability, strong adhesion to the metal substrate and to paint top coatings, if present, and typically exhibits a thickness of only about a micron or less. Corrosion testing results show that aluminum panels coated with such a submicron coating of preferred materials of this invention, without a paint top coat, can tolerate corrosive environments as described in ASTM B117, for up to 168 hours and more. To the contrary, uncoated aluminum panels begin to corrode in about six hours under this test. As a paint primer, the submicron coating of this invention provides excellent paint adhesion between metal and paint for up to about three thousand hours or more in salt spray tests, while untreated panels show high degree of paint loss in the same tests. The definition of "primer" here is two-fold. First it refers to a pre-paint treatment. Also, it can refer to an underlying coating beneath a top coating.

SUMMARY OF THE INVENTION

In an aspect, this invention is a composition which comprises the reaction product of (1) an alkylene ether polyamine containing at least a pair of primary amine groups separated from each other by at least four intermediate atoms in a chain with (2) a silane comprising silicon bonded to a plurality of hydrolyzable groups and to at least one organic epoxy radical, said silane comprising hydrolyzable silane groups, said reaction product being substantially free of unreacted epoxy groups and exhibiting an average of at least 2.5 of said hydrolyzable silane groups per molecule.

In another aspect, the present invention is a dispersion in at least one solvent of at least one compound of the general formula:

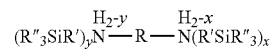

wherein R is selected from: hydrocarbon and hydrocarbon ether groups that separate the N atoms by at least four intermediate atoms in a chain; each R' group is a hydrocarbon or hydroxylated hydrocarbon ether group that separates each Si from each N by at least three carbon atoms; each R" group is a silicon-bonded hydrolyzable group or an alkyl group, at least two of said hydrolyzable groups being bonded to each Si atom; and x and y are each numbers of a value of essentially 1 to 2 that together total from 2.5 to 4.

In another aspect, the present invention is a dispersion in at least one solvent of at least one compound of the average formula:

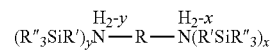

wherein R is selected from the group consisting of: alkylene and arylene groups that separate the N atoms by at least four intermediate atoms in a chain; each R' group is a hydrocarbon or hydroxylated hydrocarbon ether group that separates each Si from each N by at least three carbon atoms; each R" group is a silicon-bonded hydrolyzable group or an alkyl group, at least two of said hydrolyzable groups being bonded to each Si atom; and x and y are each numbers of a value of essentially 1 to 2 that together total at least about 3.

DETAILED DESCRIPTION OF THE INVENTION

Specifically in accordance with this invention, a method of improving paint adhesion to a metal surface is provided, which comprises: applying to a metal surface a paint primer, and drying the surface for at least partial crosslinking, wherein the primer comprises, before drying, a dispersion in one or more solvents of one or more compounds of the average formula:

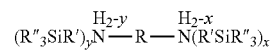

in which R is selected from the group consisting of hydrocarbon and hydrocarbon ether groups that separate the N atoms by at least four intermediate atoms in a chain; each R' group is a hydrocarbon or hydroxylated hydrocarbon ether group that separates each Si from each N by at least three carbon atoms; each R" group is independently a silicon-bonded hydrolyzable group or an alkyl group, at least two of said hydrolyzable groups being bonded to each Si atom; and x and y are each numbers of a value of essentially 1 to 2 that together total from 2.5 to 4, and preferably 2.5 to 3.5. Paint is then applied to the primed surface and drying; whereby improved paint adhesion to said surface is provided.

In some embodiments, x and y may total essentially 3.0, a level at which particularly improved paint adhesion results have been noted.

In some embodiments, R may comprise a branched alkylene radical of at least 6 carbon atoms, or an alkylene ether radical, an alkylene polyether radical, or an arylene radical.

In some embodiments, R' comprises the ring-opened residue from an organic epoxide radical, for example the 3-glycidoxypropyl radical.

R" may comprise, as stated, an alkyl group such as methyl or ethyl, but preferably all of the R" groups comprise hydrolyzable groups, such as methoxy, ethoxy, acetoxy, or the like. Also, hydroxyl is considered to be a candidate as an R" group, and is considered to be a "hydrolyzable group" for purposes of definition herein. SiR"$_3$ is defined as a "hydrolyzable silane group."

In certain embodiments, R can be a branched alkylene radical, for example, of about 9 carbon atoms, while R' is the residue of the 3-glycidoxypropyl radical, R" is methoxy or ethoxy, and x and y total about 3. This material may be as disclosed in my U.S. Pat. No. 6,867,318 B1, issued Mar. 15, 2005, the disclosures of which are incorporated by reference herein.

The primed surface may receive a paint, for example, such as acrylic paints, epoxy paints, or polyester-polyurethane paints.

In some embodiments, the metal surface which is so treated may comprise aluminum, zinc, titanium, or alloys thereof.

In another aspect of this invention, a method of improving paint adhesion to a metal surface is provided which comprises the steps of: applying to a metal surface a paint primer, and drying the surface for at least partial crosslinking, which primer comprises a dispersion in one or more solvents of the reaction product of (1) a compound comprising a polyamine in which a plurality of amine groups are bonded to at least one radical selected from the group consisting of hydrocarbon and hydrocarbon ether groups that separate nitrogen atoms of said amine groups by at least four intermediate atoms in a chain, and (2) a silane which carries a plurality of silicon-bonded hydrolyzable groups and a silicon-bonded organic group that is covalently reactive with and which bonds with said amine group, to provide a reaction product molecule which comprises an average from 2.5, and typically about 3.5 or 4 hydrolyzable silane groups per molecule; followed by the step of applying paint to the primed surface, whereby improved paint adhesion to said surface is provided.

The phrase "silicon-bonded organic group that is covalently reactive with and which bonds with said amine group" is defined as an organic group which has a moiety or portion, such as an epoxy ring, that is spaced from the silicon atom, and is covalently reactive with an amine group, to bond the silicon bonded organic group, and the silicon atom that it carries, with the molecule that carries the amine group. As shown below, an example of such a silicon-bonded organic group is 3-glycidoxypropyl. Thus, in a compound used in this invention, the silicon atom per se does not react with the amine group, but is spaced from the amine group by the silicon bonded organic group.

In some embodiments, essentially two amine groups are present per molecule of reaction product, each amine group comprising a primary amine prior to reaction with the silane. Thus, the original reactant to form the reaction product may be a diamine with two primary amine groups separated by the hydrocarbon or hydrocarbon ether groups that separate the nitrogen atoms of the amine groups, such as the R groups as described above.

In some embodiments, the polyamine may comprise about one molar part of C, C, C-trimethyl-1,6-hexane diamine (such a carbon structure is disclosed in U.S. Pat. No. 6,867,318), reacted with a silane that has bonded hydrolyzable groups and a silicon-bonded organic epoxide radical, such as 3-glycidoxypropyl-trimethoxysilane. As stated above, when about three molar parts of the silane are reacted with about one molar part of the diamine, and the metal surface comprises aluminum, particularly excellent paint priming is achieved.

When about four molar parts of the silane are reacted with one molar part of the diamine, an excellent anticorrosion agent for aluminum and other metals results, as illustrated below.

In some embodiments, the polyamine has a molecular weight in the range of 100 to 10,000. Good results can be achieved when one molar part of the diamine is reacted with at least 2.5 molar parts of the silane, to provide a composition with molecules containing both silicon and amine groups and at least 2.5 hydrolyzable silane groups per molecule, up to typically about six silane groups per molecule, on average.

Polyamines may be used having more than two amine groups per molecule for reaction with silane groups as described above, to provide at least 2.5 hydrolyzable silane groups per molecule, and preferably 3, 4, or more of such groups per molecule. For strong corrosion resistance, it is generally preferred for the total number of hydrolyzable silane groups of the product molecules to total essentially 3.5 or more, such as up to about 7. For use as a paint primer, it is generally preferred for the number of hydrolyzable silane groups to together total about 2.5 to 3.5 or 4.

Furthermore, by this invention, a method of improving corrosion resistance to a metal surface is provided which comprises: reacting (1) an alkylene ether polyamine containing at least a pair of primary amine groups separated from each other by at least four intermediate atoms in a chain, with (2) a silane having silicon atoms bonded to hydrolyzable groups and to at least one organic epoxy radical, under stoichiometry and reaction conditions where essentially all of the epoxy is reacted with amine groups, to obtain a composition with molecules containing both silicon and amine groups and at least 2.5 or three hydrolyzable silane groups per molecule, and thereafter applying a dispersion of said composition in one or more solvents to a metal surface, and drying the composition on said surface to provide a corrosion resistant coating and/or which may serve as a paint primer. The known Jeffamine materials may be used as the polyamine, to provide a product in accordance with this invention. The above method may utilize a composition which comprises a reaction product of (1) alkylene ether polyamine (which term includes polyethers) containing at least a pair of primary amine groups separated from each other by at least 4 intermediate atoms in a chain with (2) a silane comprising silicon atoms bonded to a plurality of hydrolyzable groups and to at least one organic epoxy radical. The silane thus comprises "hydrolyzable" silane groups, as defined above. The reaction product is preferably substantially free of unreacted epoxy groups, and exhibits at least 2.5, preferably 3.5 or 4 of said hydrolyzable silane groups per molecule.

Also, this composition is preferably substantially free of polysiloxane moieties of more than five connected siloxane units in length, as a result of the way the composition is synthesized this exhibits advantage in that polysiloxanes, particularly those of larger numbers of connected siloxane units, impart a strong influence on surface tension of the product which influence may be undesirable. Also, because of the use of the silanes in the synthesis process, the product, when placed on metal surface in an uncured form, has greater ability to penetrate into molecular-sized crevices and the like in the surface of the metal, to provide a stronger, more stable cured coating, which can provide improved results both as a corrosion resistant layer and as a priming layer for paint or the like.

Also this invention relates to a method of improving corrosion resistance to a metal surface, which comprises the steps of: applying to a metal surface a protective coating, and drying the surface for crosslinking, which coating comprises, before drying and crosslinking, a dispersion in one or more solvents of one or more compounds of the average formula:

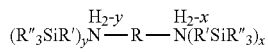

in which R is selected from the group consisting of alkylene and arylene groups that separate the N atoms by at least four intermediate atoms in a chain; each R' group is a hydrocarbon or hydroxylated hydrocarbon ether group that separates each Si from each N by at least three carbon atoms; each R" group is a silicon-bonded hydrolyzable group or an alkyl group, at least two of said hydrolyzable groups being bonded to each Si atom; and x and y are each numbers of a value of essentially 1-2 that together total at least 3, and preferably about 3.5 to 4, whereby improved corrosion resistance to said surface is provided.

This system for providing a corrosion resistant coating has the advantage that essentially all of the epoxy is reacted with amine groups, to obtain an optimum cross-linked entity and an alkylene ether chain separating the amine groups.

In some embodiments, R may be a branched alkylene radical of at least 6 carbon atoms. R' may comprise a ring opened residue from an epoxide radical. R" may comprise hydroxy or alkoxy radical of 1 to 6 carbon atoms, in some embodiments.

The metal surface may, in particular, comprise aluminum, and the polyamine may in some embodiments have a molecular weight in the range of about 100 to 10,000.

Also this invention relates to a method which comprises improving corrosion resistance to a metal surface comprising the steps of: applying to a metal surface a composition, and drying the surface for crosslinking, which composition comprises a dispersion in one or more solvents of a compound comprising the reaction product of (1) a polyamine in which a plurality of amine groups are bonded to at least one radical selected from the group consisting of alkylene and arylene groups that separate amine nitrogen atoms by at least four intermediate atoms in a chain, and (2) a silane which carries a plurality of silicon-bonded hydrolyzable groups, and a silicon-bonded organic group that is covalently reactive to said amine group, to provide a reaction product molecule which comprises an average of at least 3 and preferably at least 3.5 hydrolyzable silane groups per molecule, whereby improved corrosion resistance to said surface is provided.

In some embodiments, essentially two amine groups are present per molecule of reaction product, each amine group comprising a primary amine prior to reaction with the silane, which may typically be a glycidoxysilane.

As before, the metal surface may comprise aluminum or another metal as previously listed. The silicon-bonded hydrolyzable groups typically comprise methoxy or ethoxy.

R' may comprise, for example, a branched alkylene radical of at least 6 carbon atoms, and arylene radical, or an alkylene ether radical (which includes alkylene polyether radicals).

The compound described above may be reacted with an organic acid such as formic acid or acidic acid prior to the application to the metal surface to solubilize it. The paint primer may typically comprise water as a solvent.

Also, the above composition used as a protective coating may comprise the reaction product (1) an alkylene ether polyamine containing at least a pair of primary amine groups separated from each other by at least four intermediate atoms in a chain with (2) a silane comprising silicon bonded to a plurality of hydrolyzable groups and to at least one organic epoxy radical. The reaction product may be substantially free of unreacted epoxy groups and may exhibit at least 2.5 of the hydrolyzable silane groups per molecule, on average. Further, the composition may be substantially free of polysiloxane moieties of more than five connected siloxane units in length, and, in some embodiments, exhibits at least about 3.5 of the hydrolyzable silane groups per molecule. Polysiloxanes have a strong effect on surface tension, which may be undesirable.

Another nitrogen containing reactant which can be used to bond with silanes is a polyethylene imine with at least four ethylene repeating units spacing the nitrogen groups, which are considered as amine groups for purposes of description herein, and are usable in this invention by bonding with silanes as generally described herein.

Examples of R for the formulae described above include the hexamethylene radical from hexamethylene diamine, or the corresponding 2,2-dimethyl-4-methyl hexamethylene diamine, which may be reacted with silanes of the stated formula to provide a hydrolyzable, cross-linkable compound described above. Tetramethylene diamine may also be used, to provide an R group, which is the tetramethylene radical. Broadly, the diamine used in this invention may be of the formula $H_2N$—$(CR_1R_2)_{z2}N$—$H_2$, where z is an integer from 4 to 22, and $R_1$ and $R_2$ are independently hydrogen or branched hydrocarbon radicals containing up to 4 carbon atoms. The R group is the radical that remains when amine groups are deleted from the above.

Aromatic polyamine materials may be used, where $R_1$ through $R_8$ of these aromatic formulations may comprise hydrogen or lower alkyl groups up to about 6 carbon atoms. These polyamines may be respectively reacted with the hydrolyzable silanes described herein to provide the polyfunctional, cross-linkable materials used in this invention. Examples are shown below:

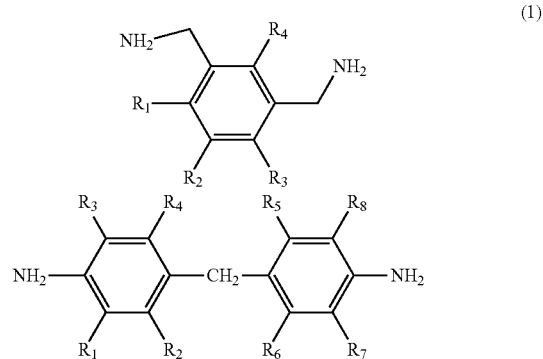

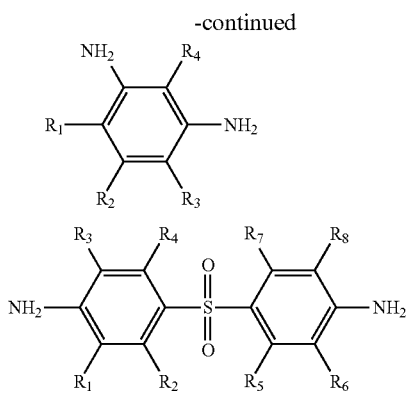

As another category of polyamines which may be used in this invention, providing a hydrocarbon ether or polyether R group with at least two attached amine groups, is shown below. Jeffamine-type materials may also be used to form the R group.

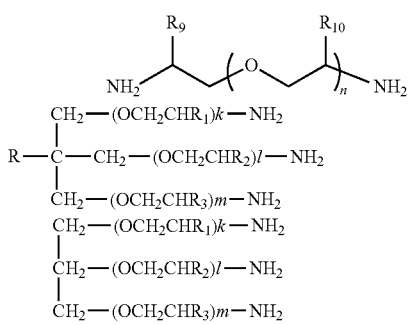

(2)

As used in the formulas immediately above, n, k, l and m are independently integers from 1 to 3,000. In the formulae above, $R_1$ through $R_{10}$ may independently be hydrogen or organic groups of up to 4 carbon atoms. Typically, each of the numbered R groups in the groups of formulas (1) and (2) immediately above may be hydrogen.

Other examples of aromatic diamines and polyamines, for reaction with the polysilanes described herein (thus forming an R group that links amine groups) are as follows:

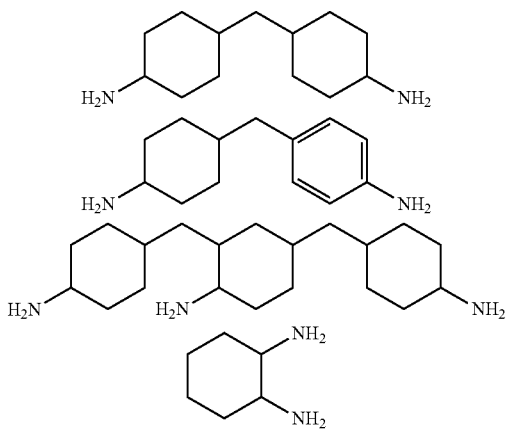

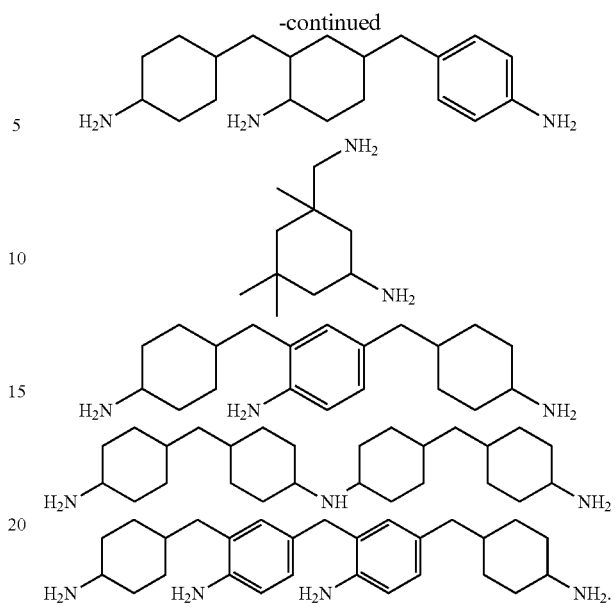

In the reaction of a polyamine with the silane carrying silicon-bonded hydrolyzable groups as described above, the multifunctional amine "backbone", represented by R above covalently links through the amine groups to the silane "arms" (the R' groups) as above, to form amine silane adducts. In the embodiments where an epoxy silane is used, the adducts are formed by the creation of amine-epoxy linkages, with a varying number of the amine-epoxy linkages depending on the molar ratio, to provide differing effects as described above. The resulting silane-modified amine adducts thus carry multiple terminal silyl groups that are bonded to hydrolyzable groups such as alkoxy. These are capable of high-degree, intermolecular cross-linking by hydrolysis and linking of the hydrolyzable groups as the material is cast from a solution or dispersion and cured into a crosslinked, corrosion protecting film. Excellent results have been achieved in protecting painted and unpainted aluminum alloys, exhibiting an overall performance that can be comparable to chrome-based conversion coatings.

The polyamine-epoxy silane adducts are water-soluble or water dispersible especially when neutralized with an organic acid such as acetic acid. Therefore the technology can be compliant with low VOC emission regulations. Also, the coating solution is free of hazardous metals such as chromium. Furthermore, an aqueous 5% solution of a preferred polyamine silane adducts exhibits a long tank life of greater than three weeks without degradation of anticorrosion performance, indicating the hydrodynamic stability of particularly the amine-epoxy silane adducts in water. Thus, the process of use of the materials of this invention can be fully compatible with the existing equipment of customers.

The coating can be applied to metal substrates such as aluminum and alloys thereof from water solution, either by spraying, dipping, or the like. The entire process may be accomplished by an initial step of alkaline cleaning, a double rinse, dip coating, and curing by annealing with drying. Typical annealing temperatures range from room temperature of about 20° C. to an elevated temperature of about 120° C., with higher temperatures accelerating the cross-linking process of the coating.

The reaction conditions for making polyamine-epoxy silane adducts are generally quite mild. For the epoxy silanes the conditions of making adducts may often be simply a period of reaction of 24 to 48 hours at about 22° C., or a period of about 3 hours at 70° C., the reaction being typically performed in alcohol solvent. The reaction yield is high, usually exceeding 90% of the amine present.

The resulting coating provided is thin and clear, being typically on the order, after drying, of 0.3 to 1 micron in thickness (in the case where it is dip-coated from 5 weight percent water solution). The material of this invention is thus invisible to the eyes, and therefore does not interfere with the metal's natural luster, contrary to the chromium based conversion coatings.

Examples of epoxy silanes which may be used in this invention comprise 3-glycidoxypropyltrimethoxysilane: 3-glycidoxypropylmethyldimethoxysilane; 3-glycidoxypropyltriethoxysilane; and 3-glycidoxypropylmethyldiethoxysilane.

A preferred solvent for conducting the adduct-forming reaction is alcohol or alcohol-containing solvent in which the alcohol content is 30% by volume or more, typically about 50 volume percent. The preferred alcohols are the alkyl alcohols, linear or branched, of no more than 6 carbon atoms, specifically methanol or ethanol, particularly when using a water-based working solution.

The preferred synthesis temperature may typically range from about 70° F. to 250° F. Higher temperatures generally give faster reaction kinetics. In a typical reaction that uses methanol as a solvent without pressure, the reaction temperature may be held constant at the boiling point of methanol, 150° F., for up to about 6 hours. Using a reaction vessel that can sustain pressure can bring the reaction temperatures higher than the point of boiling alcohol, thus achieving faster reaction rate at 200° F. and 5 atmosphere pressures.

The reaction in methanol between the epoxy silane and the polyamine can go to completion with greater than 90% yield in 3 hours.

The prepared reactant loading in the total solvent-reactant mixture is generally not critical, and thus may range from about 1-95%. More preferred reactants are on the order of 70% of the total weight of the mixture, or less.

The resulting multifunctional amino silane produced can be applied, with or without further dilution with organic solvent, as a solvent-borne coating onto metallic substrates. Typically, the multifunctional silane will be at least partially hydrolyzed into silanol form. This partial hydrolysis can be achieved by adding a small amount of water to the multifunctional silane-alcohol solvent mixture, or the water may be present in the reaction mixture initially. For a silane-solvent 50:50 mixture by weight, it is preferred that about 2 to 5 parts by weight of water should be present for every 100 parts by weight of the polyamine-silane adduct.

As a preferred method for dissolving the multifunctional polyamine-silanes in water, which may be required in certain situations where high volatile, organic solvent emissions are undesirable, the multifunctional polyamine-silane may be converted into the ammonium or salt form with acids. The preferred acids are volatile organic acids with a boiling point less than 350° F. including but not limited to acetic acid and formic acid.

For use as a paint primer, the preferred polyamine-silane may be applied in about a 0.01 to 10% by weight concentration, for example a concentration of about 0.2 to 5 weight percent. When the material is used as an anticorrosion agent and not as a paint primer, the preferred concentration in the working solution may be about 0.1 to 30% by weight, particularly about 2 to 10% by weight.

The polyamine-silane can be applied to metal parts, sheeting, or the like by dipping or spraying, or also by wiping, a fog chamber, or an aerosol chamber. The contact time between the polyamine-silane dispersion or solution and the metal parts should typically be at least one second, and typically there is no subsequent rinsing. The surface is allowed to dry and to stand, optionally at elevated temperature to accelerate the crosslinking process between the silane groups by hydrolysis of the hydrolyzable groups and formation of siloxane linkages. A desired catalyst may be present to facilitate the crosslinking process and siloxane formation if desired. The applicable catalyst is selected from the group consisting of effective acids, bases, and organometallic compounds. The applied polyamine-silane coatings should be cured by the formation of the siloxane linkages (Si—O—Si) between the various silane groups of different molecules to form crosslinking, as is a known process. The indication of a cured, multi-functional polyamine-silane film is that the film is no longer soluble in water or in an organic solvent.

The curing or crosslinking of the polyamine-silane film maybe simply to allow evaporation of the solvent from which the silane is applied with the crosslinking taking place spontaneously upon drying, either at ambient or elevated temperature, with a relative humidity optionally present to provide water vapor that may participate in the reaction with the hydrolyzable groups in a known manner. When the polyamine-silane coating is being used as an anti-corrosion layer, a full cure is preferred for optimum corrosion protection by, for example, heating coated parts at 160° F. to 400° F. for 3-30 minutes, although other curing (crosslinking) conditions may be used as desired. However, when the material is being used as a primer for paint on a metal surface, a full cure may not be necessary.

As previously stated, numerous metal surfaces may exhibit benefit when the polyamine-silane coating is applied in accordance with this invention, for example surfaces of aluminum, zinc, copper, iron, titanium, nickel, and alloys containing the above metals, including but not limited to steel, galvanized steel, and aluminum-zinc steel.

The metal parts to be treated with the polyamine-silane of this invention preferably have clean surfaces, i.e. surfaces that are free of dirt, grease, oil or other contaminants, but the native oxide layer present on aluminum and many other surfaces may not be viewed as a contaminant, and may remain, if desired. A preferred method of cleaning is to subject the metal parts to a cleaning bath either by spray or dipping, or by manual wiping to clean. For treating metal with a water-borne polyamine-silane solution as in this invention, the metal should be cleaned to the point of being "water-break-free" (i.e., water that is added to the surface spreads completely to form a uniform and contiguous water film among the metal surface) rather than beading up.

Surface active agents may be optionally added to improve the wetting of the polyamine-silane solution on a metal surface. Anionic, cationic, and nonionic surfactants can be added to the film forming material in a concentration of typically 0.05-2 weight percent of the total solution weight. Anionic or nonionic surfactants are typically preferred. Deformers may also be added, typically at a weight percent of about 0.1-3 percent, based on the total solution weight.

Corrosion inhibitors may also be added, including both cathodic and anodic inhibitors, optionally in the amount of 0.1-5 weight percent of the polyamine-silane ingredient present. Preferred corrosion inhibitors comprise water soluble nitrates, nitrites, phosphates, pyrophosphates, molybdates, cerium salts, zinc salts, azoles, azole salts, imidazolines fatty amines, sulfides, and aromatic amines.

The above disclosure and the examples below are offered for illustrative purposes only, and are not intended to limit the scope of the invention of this application, which is as defined in the claims below.

EXAMPLE 1

A 4:1 molar ratio of 3-glycidoxypropyltrimethoxysilane and C,C,C-trimethyl-1,6-hexanediamine (in favor of the silane) is added to an equal weight of ethyl alcohol. The alcohol used in this invention generally contains some water such as 0.5 wt. percent. The mixture is allowed to react at 70° C. for three hours. The reaction products are subsequently neutralized with a 20% excess (based on stoichiometry) of acetic acid. This multifunctional silane is referred to as TG14 hereafter, the molecules of the adduct polyamine-silane having about an average of four bonded silane groups.

Corrosion protection of unpainted aluminum alloys by the material TG14 was tested by the conditions of ASTM B117 salt spray. A 5 weight percent solution or dispersion of TG14 in water was applied to various panels of various aluminum alloys. The resulting film on the alloy of diamine-silane was dried in a baking oven at 250° F. for twenty minutes. Then, the various panels were placed into contact with a continuous salt spray and the time measured without showing visible corrosion (i.e. pitting or corrosion of an area greater than 0.1 percent of the panel area corroded), measured in days. Aluminum 3105 alloy withstood 10 days of such salt spray; aluminum 2024 alloy withstood 3 days, and aluminum 3003 alloy withstood 14 days. This is to be compared with uncoated aluminum panels, which withstood zero days, and a commercial chromate coating, which respectively withstood 14 days for 3105 alloy, 7 days for the 2024 alloy, and 14 days for the 3003 alloy.

EXAMPLE 2

A mixture of 3-glycidoxypropyltrimethoxysilane and C, C, C-trimethyl-1,6-hexanediamine at a 3:1 molar ratio in favor of the silane was added to an equal weight of methyl alcohol, with stirring. The mixture was allowed to react at 60-80° C. for about 3 hours or, alternatively, at room temperature for about 48 hours. The reaction products are subsequently neutralized with a 20% excess (based on stoichiometry of acetic acid. This multifunctional silane is referred to as TG13 hereafter.

Upon application to aluminum panels in a manner similar to Example 1, anticorrosion effect to a lesser degree from that of Example 1 was seen relative to the 3105 alloy and the 3003 alloy.

A. However, panels of aluminum alloy 1100 and 6061 were respectively treated with 1% water solutions of TG13 and TG14 (Examples 2 and 1) and allowed to conventionally cure with ten minutes exposure to air at 160° F. Following this, the cured panels were respectively powder coated to a depth of 0.003" with epoxy resin (PPG PCM 10114), and were conventionally cured to provide a cured epoxy coating. After a 1,000 hour salt spray under conditions as described in Example 1, the panels of 1100 aluminum alloy treated with TG13 showed an average under-paint creepage of 0.5 mm, but while those treated with TG14 showed an average under-paint creepage of 1.0 mm. On the aluminum 6061 alloy panels, those treated with TG13 also had an average under-paint creepage of 0.5 mm, while TG14-treated panels showed an average under-paint creepage of 2.5 mm.

B. Also, in another test, aluminum panels of alloy 1100 and 2024 were pre-treated as in the paragraph above respectively with 1% water solutions of TG13 and TG14. After crosslinking and similar drying, the panels were powder-coated with 0.003" of polyacrylate resin (PPG PPC 10103H). After a 1,000 hour salt spray for these panels under the conditions of Example 1, the 1100 alloy panels treated with TG13 exhibited essentially zero under-paint creepage, while those treated with TG14 showed an average under-paint creepage of 0.5 mm. On the 2024 alloy panels, the TG13-treated panels exhibited an average under paint creepage of 1 mm, while the TG14-treated panels exhibited an average under paint creepage of 3.5 mm.

C. Aluminum panels of 7075 alloy were pre-treated respectively with a 0.5% solution of TG13 or TG14, and thereafter allowed to dry for curing under the conditions of Section A above. The panels were then powder coated to a thickness of 0.003" with polyurethane resin (Rhom and Haas 23-9030) and allowed to cure in accordance with the recommended manner. Following this, a 1,000 hour salt spray was applied to the panels as in Example 1. For said period, the 7075 alloy panels treated with TG13 exhibited an average blister size of 2.0 mm, while those treated with TG14 exhibited an average blister size of 4.0 mm.

D. Hot-dipped galvanized steel panels were respectively pre-treated with 2.5 weight percent aqueous solutions of TG13 and TG14, the solutions being adjusted to pH 6.0 with ammonium hydroxide. Following drying, the panels were painted to a thickness of about 20 microns with white polyester paint (Sherwin-Williams Permaclad). The painted panels were then baked at 350° F. for 15 minutes to reach full curing. The panels were subjected to salt spray for 7 days in accordance with Example 1 and evaluated for under-paint creepage, as before. The panels treated with TG13 exhibited an average creepage of 0.5 mm. The panels treated with TG14 exhibited an average creepage of 2.5 mm. A similar panel painted with the white polyester paint but without a coating of diamine-silane had 11 mm of creepage.

Accordingly, it can be seen that while TG14 (Example 1) is superior as a corrosion resistant agent for metal, TG13 of this Example is superior as a paint primer, including powder coatings as described above.

E. Panels of aluminum alloys 3003, 3105, 5086, and 1100 were brought into contact respectively with 5% freshly hydrolyzed aqueous solutions of TG13 and TG14, followed by oven baking at 250° after 20 minutes. The baked panels were then salt sprayed as in Example 1 for 14 days, and evaluated for the respective corrosion of each. The panels treated with TG13 started to show corrosion as early as 48 hours, while those treated with TG14 showed essentially no signs of corrosion after 336 hours of salt spray.

EXAMPLE 3

A mixture of 3-glycidoxypropyltrimethoxysilane and 1,10-decanediamine at a 4:1 molar ratio in favor of the silane was added to an equal weight of methyl alcohol, with stirring. The mixture was allowed to react at about 60-80° C. for about 3 hours, or alternatively at room temperature for about 48 hours. This multifunctional silane is referred to as DG14.

An aluminum 2024 alloy panel was coated and tested in the manner of Example 1 for corrosion using DG14. The coated panel with DG14 withstood three days of salt spray treatment, compared with zero days for a coating free corresponding aluminum panel, and 7 days for a conventional commercial chromate coating.

EXAMPLE 4

A mixture of 3-glycidoxypropyltrimethoxysilane and 1,5-pentanediamine was mixed at a 4:1 molar ratio in favor of the silane, and added to an equal weight of methyl alcohol, with stirring. The mixture was allowed to react at 60-80° C. for 3 to 16 hours, or at room temperature for 48 hours, to provide a diamine-silane adduct containing about 4 silane groups per molecule. The mixture exhibits anticorrosion characteristics, when coated onto a metal sheet and allowed to dry with crosslinking.

EXAMPLE 5

A mixture of 3-glycidoxypropyltrimethoxysilane and 1,22-docosanediamine at a 4:1 molar ratio in favor of the silane is added to an equal weight of methyl alcohol, with stirring. The mixture is allowed to react for about 3-16 hours at 60-80° C., or at room temperature for 48 hours. The material imparts corrosion protection to metals.

EXAMPLE 6

A mixture of 3-glycidoxypropyltrimethoxysilane and 1,3-xylenediamine at a 4:1 molar ratio in favor of the silane was added to an equal weight of methyl alcohol, with stirring. The mixture was allowed to react at 60° C. for 16 hours.

The resulting adduct, referred to as XG14 hereinafter, was applied to a panel of aluminum 2024 alloy and allowed to dry for crosslinking. The panel was subjected to the ASTM B117 salt spray, and endured 4 days without showing visible corrosion.

EXAMPLE 7

A mixture of 3-glycidoxypropyltrimethoxysilane and methylenedianiline at a 4:1 molar ratio in favor of the silane was added to an equal weight of n-butyl alcohol, with stirring. The mixture was allowed to react at 120° C. for 16 hours.

EXAMPLE 8

A mixture of 3-glycidoxypropyltrimethoxysilane and a polyethertriamine (Jeffamine T-403 of Huntsman Corporation) was mixed at a 6:1 molar ratio in favor of the silane, being added to an equal weight of methyl alcohol, with stirring. The mixture was allowed to react at 60° C. for 5 hours. This multifunctional silane is referred to below as JG16.

This was applied to panels of aluminum 2024 alloy and aluminum 3003 alloy and allowed to dry and cure by crosslinking. The panels were then exposed to the ASTM B117 salt spray corrosion test. The 2024 alloy showed no corrosion for 3 days. The 3003 alloy panel showed no corrosion for 14 days.

EXAMPLE 9

A mixture of 3-glycidoxypropyltrimethoxysilane and tetraethylenepentamine at a 7:1 molar ratio in favor of the silane was added to an equal weight of methyl alcohol, with stirring. The mixture was allowed to react at 60° C. for 5 hours to provide an adduct which provides anticorrosion characteristics when applied to an aluminum panel.

EXAMPLE 10

A mixture of glycidoxypropyltrimethoxysilane and bis(hexamethylene)triamine at a 5:1 molar ratio in favor of silane was added to an equal weight of methyl alcohol, with stirring. The mixture was allowed to react at 60° C. for 5 hours. When applied to aluminum sheeting and allowed to dry, corrosion resistance is noted.

EXAMPLE 11

The TG14 material of Example 1 was neutralized with a 20% stoichiometric amount of acetic acid, followed by dilution with water to a 5 weight percent content of the diamine-epoxy silane product. This material was applied to aluminum panels by dip coating or spraying, with the panels being cured at 120° C. for one-half hour. The coated aluminum derived in this manner exhibits outstanding corrosion protection. Specifically, panels of aluminum 2024 alloy treated in this manner can tolerate over 100 hours of salt spray by ASTM B117 without showing any signs of corrosion, while bare aluminum panels start to corrode in about 6 hours. When the material of this example is to be used as a paint primer, a one weight percent concentration is suitable.

EXAMPLE 12

The clear solution of Example 11 may also contain 0.1 weight percent of cerium nitrate; 0.1 weight percent of Surfynol 465 surfactant-defoamer (sold by Air Products); 0.5 percent of an aluminum-coated colloidal silica of 20 nm average diameter (Nalco TX11678) and 0.5 weight percent of a polyacrylate polymer, with the silane concentration being about 5 weight percent.

EXAMPLE 13

The diamine-epoxy silane adduct of Example 1 was allowed to stand in the presence of a small amount of water in solution, normally present in the alcohol, for partial hydrolysis thereof. The alcohol/diaminoepoxysilane is then directly applied without further water dilution to aluminum panels and cured as a film on the panel for half an hour at 120° C., to provide a corrosion resistant surface.

The isopropanol dispersion or solution containing 5 weight percent of hydrolyzed TG14 that resulted was placed on aluminum panels and allowed to cure as described above. Aluminum 2024 alloy panels withstood 5 days of ASTM B117 salt spray testing without corrosion; aluminum 3003 alloy panels withstood 16 days of such salt spray testing without sign of visible corrosion. As stated above, untreated aluminum panels being corrosion in the salt spray tester in less than a day, typically about 6 hours.

EXAMPLE 14

The formulation of Example 1 had about 0.1 weight percent of cerium nitrate added, being a 5 percent aqueous solution, based upon the diaminopolysilane present. The solution was applied to aluminum panels by dipping or spraying, and allowed to dry and cure for crosslinking. Panels of aluminum 2024 alloy treated in this manner exhibited 5 days of ASTM B117 salt spray testing without visible corrosion. Panels made of aluminum 3003 alloy exhibited 21 days of such salt spray testing without corrosion.

EXAMPLE 15

The TG13 material of Example 2 was diluted down to a 1 weight percent water solution and applied to aluminum 2024 alloy panels by spraying or dip coating. The resulting film was allowed to dry at room temperature for 15 minutes. Then, the treated panels were subsequently painted with about a 20 micron thick layer of polyurethane water borne paint (Wood Classic of Sherwin-Williams Co.) following which the panels were baked at 300° F. for 20 minutes. The resulting cured panels were scribed with a blade before being treated by salt spray in accordance with ASTM B117. After 700 hours of salt spray, no paint loss was observed on the treated panels along the scribed line, while untreated panels exhibited more than a 10 mm loss (under paint creepage) of paint along the lines.

EXAMPLE 16

The alcohol-based TG13 product of Example 2 was applied by spraying or dip coating two aluminum panels. When paint is applied to the panels, with drying allowed, and scribed, as in Example 15, the salt spray results obtained are substantially similar to those obtained from the water-based procedure of Example 16.

EXAMPLE 17

Products respectively of Example 1 (TG14), Example 2 (TG13) and Example 8 (JG16) were each diluted to about one percent of multifunctional silane and applied to aluminum 2024 alloy panels. After being allowed to dry they were painted and, after further cure, were subjected to 14 days of ASTM B117 salt spray, having previously had scribed lines formed to expose a linear aluminum surface.

After such treatment, all of the panels described above exhibited paint loss (creepage) of essentially 0.5 mm width along the scribed line. A similar aluminum panel without a polyamine-polysilane primer coating exhibited under paint creepage (paint loss) of 10 mm transversely across the scribed line.

EXAMPLE 18

The product of Example 2, TG13, was diluted with water to form a 2% solution. The pH was adjusted to 6.5 with ammonia. The resulting solution was applied to hot-dipped galvanized steel (90G ACT Laboratories) and dried at 160° F. for 5 minutes. The polyamine-silane treated panels were subsequently painted with white polyester paint of Sherwin-Williams Co. The painted panels were baked at 350° F. for 20 minutes.

The panels were then scribed with a sharp metal tip before the salt spray testing, performed under ASTM B117. No paint loss was observed along the scribed lines after 160 hours of salt spray, while unprimed panels exhibited more than an 11 mm paint loss along similar scribed lines.

EXAMPLE 19

A mixture of 3-glycidoxypropyltrimethoxysilane and 1,3-phenyldiamine at a 4 to 1 molar ratio favoring the silane was dissolved in N-butanol of an equal weight to make a 50% solution. The solution was then held under reflux at 250° F. for five hours with stirring and a dry nitrogen atmosphere. The solution was allowed to cool down to room temperature, the reaction product was designated AG 14 and was present in the butanol solvent at about 50 wt. percent.

Ten percent by weight of this solution was mixed sequentially with 89.5% isopropyl alcohol and 0.5 wt. percent water under stirring for 5 minutes. This solution was coated onto panels of aluminum alloy 2024-T3 (obtained from ACT Laboratories) by dipping of the aluminum panel into the solution for at least one second. The panel was then dried in a baking oven at 250° F. for about fifteen minutes.

The panel coated with AG 14 in alcohol solution was then tested with the salt spray test of ASTM B117 as described in Example 1, and endured for ten days prior the onset of signs of corrosion. A corresponding conventional chromate coating on aluminum 2024 alloy lasted for only seven days before the onset of corrosion.

EXAMPLE 20

Panels of aluminum alloys 3003, and 2024 were brought into contact respectively with 5% isopropyl alcohol solutions of hydrolyzed TG14 with 0.1% cerium nitrate additive, followed by oven baking at 250° after 20 minutes. The baked panels were then salt sprayed as in Example 1 for 21 days, and evaluated for the respective corrosion of each. The panels treated with the above solution essentially show no signs of corrosion for 3003 panels after 504 hours of salt spray, and no corrosion for 2024 panels after 120 hours of salt spray.

The claimed invention is:

1. A dispersion in at least one solvent of at least one compound of the general formula

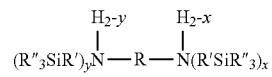

wherein R is selected from hydrocarbon and hydrocarbon ether groups that separate the N atoms by at least four intermediate atoms in a chain; each R' group is a hydrocarbon or hydroxylated hydrocarbon ether group that separates each Si from each N by at least three carbon atoms; each R" group is a silicon-bonded hydrolyzable group or an alkyl group, at least two of said hydrolyzable groups being bonded to each Si atom; and x and y are each numbers of a value of essentially 1 to 2 that together total on average from 2.5 to 4.

2. The composition of claim 1, wherein R is selected from the group consisting of:
a branched alkylene radical of at least six carbon atoms, an alkylene ether radical; an arylene radical; and an alkylene polyether radical.

3. The composition of claim 1, wherein R' comprises a ring-opened residue from an organic epoxide radical.

4. The composition of claim 1, wherein R is a branched alkylene radical, R' is the residue of a 3-glycidoxypropyl radical, and R" is methoxy or ethoxy, and x and y total about 3.

5. The composition of claim 1, wherein R" is hydroxy or an alkoxy radical of 1 to 6 carbon atoms.

6. The composition of claim 1, wherein said silicon-bonded hydrolyzable groups comprise methoxy or ethoxy.

7. A dispersion in at least one solvent of at least one compound of the average formula:

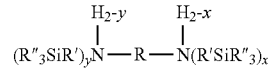

wherein R is selected from the group consisting of: alkylene and arylene groups that separate the N atoms by at least four intermediate atoms in a chain; each R' group is a hydrocarbon or hyrdroxylated hydrocarbon ether group that separates each Si from each N by at least three carbon atoms; each R″ group is a silicon-bonded hydrolyzable group or an alkyl group, at least two of said hydrolyzable groups being bonded to each Si atom; and x and y are each numbers of a value of essentially 1 to 2 that together total on average 3 to 4.

8. The dispersion of claim 7, wherein x and y are each numbers of a value of essentially 1 to 2 that together total on average about 3.5 to 4.

* * * * *